US011064599B1

United States Patent
Khalilzad-Sharghi et al.

(10) Patent No.: US 11,064,599 B1
(45) Date of Patent: Jul. 13, 2021

(54) VACUUM OIL PURIFICATION SYSTEM

(71) Applicant: Medical Imaging Solutions USA, LLC, Woodstock, GA (US)

(72) Inventors: Vahid Khalilzad-Sharghi, Woodstock, GA (US); Jeremy David Hooper, Stockbridge, GA (US); Farzad Sadeghi Tohidi, Kennesaw, GA (US); Arnold Bates, Woodstock, GA (US)

(73) Assignee: MEDICAL IMAGING SOLUTIONS USA, LLC, Woodstock, GA (US)

( * ) Notice: Subject to any disclaimer, the term of this patent is extended or adjusted under 35 U.S.C. 154(b) by 835 days.

(21) Appl. No.: 15/341,564

(22) Filed: Nov. 2, 2016

Related U.S. Application Data (60) Provisional application No. 62/387,852, filed on Jan. 12, 2016.

(51) Int. Cl.
  *H01J 35/08* (2006.01)
  *H05G 1/02* (2006.01)
  (Continued)

(52) U.S. Cl.
  CPC .............. *H05G 1/025* (2013.01); *B01D 35/02* (2013.01); *H05G 1/04* (2013.01); *A61B 6/4488* (2013.01)

(58) Field of Classification Search
  CPC ...... A61B 6/447; A61B 6/4488; H05G 1/025; H05G 1/04; G05G 1/02; H01J 2235/00;
  (Continued)

(56) References Cited

U.S. PATENT DOCUMENTS 3,954,611 A * 5/1976 Reedy .................. C10M 175/00
  210/695
4,646,793 A * 3/1987 Sherratt .............. A47J 37/1271
  137/358

(Continued)

*Primary Examiner* — Don K Wong
(74) *Attorney, Agent, or Firm* — Ballard Spahr LLP (57) ABSTRACT

Herein disclosed in a vacuum oil purification system which includes a fresh oil vacuum chamber, an old oil vacuum chamber for degasifying and dehumidifying insulating oil, a vacuum pump for generating vacuum environment, an oil pump for circulating oil, an oil filter for removing particles from oil, a pressure vessel for generating and adjusting oil pressure, heaters, heat, pressure and vacuum sensors, an oil penetration tray, a control panel having all the control buttons, LEDs, and quick connects, a mobile platform to hold all components in place, and an oil pan to collect all oil drips. A control unit with an LCD supervises all the input signals from sensors and generates command signals. The fresh oil vacuum chamber is covered by a foam and foil wrap insulation for heat exchange separation. This insulation cover dampens sound and vibration as well. The chambers have oil drain valves at the bottom. Vacuum is generated by a vacuum pump and is controlled manually by a switch and a vacuum gauge for each chamber. The vacuum is also controlled by a vacuum sensor coupled with electronics and the control unit to toggle vacuum pump on and off automatically.

The entire system including the electronics may be mounted on a four-wheel platform to facilitate transport to a job site for example a healthcare center. Apparatus for purifying the insulating oil while flushing includes a spin-on filter to clean insulating oil in the return line.

15 Claims, 10 Drawing Sheets

(51) Int. Cl.
 *B01D 35/02* (2006.01)
 *H05G 1/04* (2006.01)
 *A61B 6/00* (2006.01)

(58) Field of Classification Search
 CPC ........... H01J 2235/12; H01J 2235/1216; H01J 2235/1262; H01J 2235/1266; H01J 2235/127; H01J 2235/1275; H01J 2237/00; H01J 2237/038; H01J 2237/18; H01J 2237/182; H01J 2237/166; H01J 2237/1825; H01J 2237/184; H01J 2237/188; H02J 2235/1279
 See application file for complete search history.

(56) References Cited

U.S. PATENT DOCUMENTS

| | | | | |
|---|---|---|---|---|
| 4,869,346 A * | 9/1989 | Nelson | ............... | F01M 11/0458 184/1.5 |
| 5,330,636 A * | 7/1994 | Reichert | ................ | B01D 37/00 184/108 |
| 5,353,760 A * | 10/1994 | Zager | ................. | F01M 11/0458 123/196 A |
| 5,390,762 A * | 2/1995 | Nelson | ................ | F01M 11/0458 123/196 S |
| 5,440,608 A * | 8/1995 | Peralta | ..................... | H05G 1/04 378/141 |
| 5,516,969 A * | 5/1996 | Krasznai | ................... | G21F 9/06 208/251 R |
| 5,562,181 A * | 10/1996 | Elkin | ................ | F01M 11/0458 123/196 R |
| 5,596,622 A * | 1/1997 | Peralta | ..................... | H05G 1/04 378/130 |
| 5,732,123 A * | 3/1998 | Peralta | ..................... | H05G 1/04 378/199 |
| 5,951,857 A * | 9/1999 | Osborne | ................ | B01D 29/15 210/167.02 |
| 6,041,802 A * | 3/2000 | Nelson | ................ | A47J 37/1271 137/14 |
| 6,254,272 B1 * | 7/2001 | Dilick | ..................... | H05G 1/04 378/130 |
| 6,254,790 B1 * | 7/2001 | King | ................... | A47J 37/1223 210/767 |
| 6,273,031 B1 * | 8/2001 | Verdegan | ........... | F01M 11/0458 123/1 A |
| 6,604,856 B2 * | 8/2003 | Baumgartner | ........... | H05G 1/04 378/200 |
| 6,792,983 B2 * | 9/2004 | Allora | ................. | A47J 37/1223 141/18 |
| 7,926,617 B2 * | 4/2011 | Lockwood | ......... | F01M 11/0458 123/196 R |
| 7,938,959 B1 * | 5/2011 | Inman | ................. | A47J 37/1233 137/206 |
| 9,253,863 B2 * | 2/2016 | Bowlsbey | ............ | F01P 11/0276 |
| 9,374,878 B2 * | 6/2016 | Bowlsbey | ............. | H05G 1/025 |
| 2001/0017908 A1 * | 8/2001 | Dilick | ................. | H05G 1/04 378/200 |
| 2002/0196905 A1 * | 12/2002 | Baumgartner | ........... | H05G 1/04 378/200 |
| 2009/0283363 A1 * | 11/2009 | Lockwood | ............ | F01M 11/0408 184/1.5 |
| 2015/0101972 A1 * | 4/2015 | Coco | ................... | A47J 37/1223 210/167.28 |
| 2015/0265955 A1 * | 9/2015 | Kanchi | ................. | B01D 37/03 210/728 |
| 2017/0239596 A1 * | 8/2017 | Sequeira | ............... | B01D 29/52 |

\* cited by examiner

VACUUM OIL PURIFICATION SYSTEM

CROSS REFERENCE TO RELATED APPLICATIONS

This application claims the benefit of priority under 35 U.S.C. § 120 to U.S. Provisional Patent Application No. 62/387,852 filed Jan. 12, 2016. The prior application is incorporated herein by reference in its entirety for all purposes as if fully set forth herein.

BACKGROUND OF THE INVENTION

Field of the Invention

Embodiments described herein of the present invention relate to field of X-ray tube maintenance, specifically to a system and method of exchanging and/or purifying insulating oil used in an X-Ray Tube Assembly, particularly, but not limited to the field of computed tomography (CT) and X-ray radiography in order to extend the life of the X-ray tubes.

Background

The present invention relates to methods and devices for extending the life of an X-ray tube. Typically X-Ray tubes are mounted inside a lead shielded radiation enclosure called a housing or casing. The housing is attachable to installable in or enclosable in the X-Ray scanner, typically a Computer Tomography (CT), fluoroscopic, or X-Ray machine. The housing is filled with a fluid of synthetic or petroleum derivative, generally referred to as insulating oil. The insulating oil acts to thermally and electrically insulate the tube. All such fluids may be damaged or degraded by various factors such as heat, radiation, high voltage arcing and corona discharge.

In a CT device, the X-Ray tube generates radiation passing through the subject assigned for imaging and installed on the gantry for the purpose of revolution. The detector assembly includes an array of detectors with purpose of changing radiation to electrical signals. The high voltage (HV) transformer is a device that alters the voltage of incoming electricity to a series of high voltage (HV) pulses needed for the X-Ray generation. There is a circular channel with a gaseous coolant between the stationary platform and the gantry as well as a conduit with a circulating coolant exposed to heat generating components so that the generated heat can be eliminated from the system. The cooling procedure happens through a closed circulation system to avoid contaminating the environment around the imaging apparatus. The X-Ray source or called here X-Ray tube, which is the heart of the X-Ray generating system, consists of radiation shielded housing, an X-Ray window, a central rotary part including anode and cathode, filament, ball bearings, a rotation source, heat and pressure sensors and electrical signal terminals. The housing is filled by an insulating liquid, generally a type of mineral or synthetic oil. The X-Ray tube assembly is attached to diagnostic medical imaging modalities such as computed tomography, radiography, fluoroscopy, mammography, catheter lab and angiography. The role of the insulating oil is to electrically insulate components inside the tube in addition to cooling purposes in conjunction with a heat exchanger. During the X-Ray tube operation, the insulating oil is exposed to heat, X-Ray radiation, and high voltage arcing. Degradation of oil increases in temperatures above 140° C. based on previous studies. Oxygen, and water content also accelerate the rate of aging of insulating oil.

A method according to the principles of the present invention replaces the aging oil in an X-Ray generating system to extend the useful life of the X-Ray generating system without taking the X-Ray generating system out of service for an extended period of time. That is, the disclosed method can be performed on-site within a matter of hours, in place of the conventional removal of the X-Ray tube assembly and shipment to a service facility.

Figure 1A:
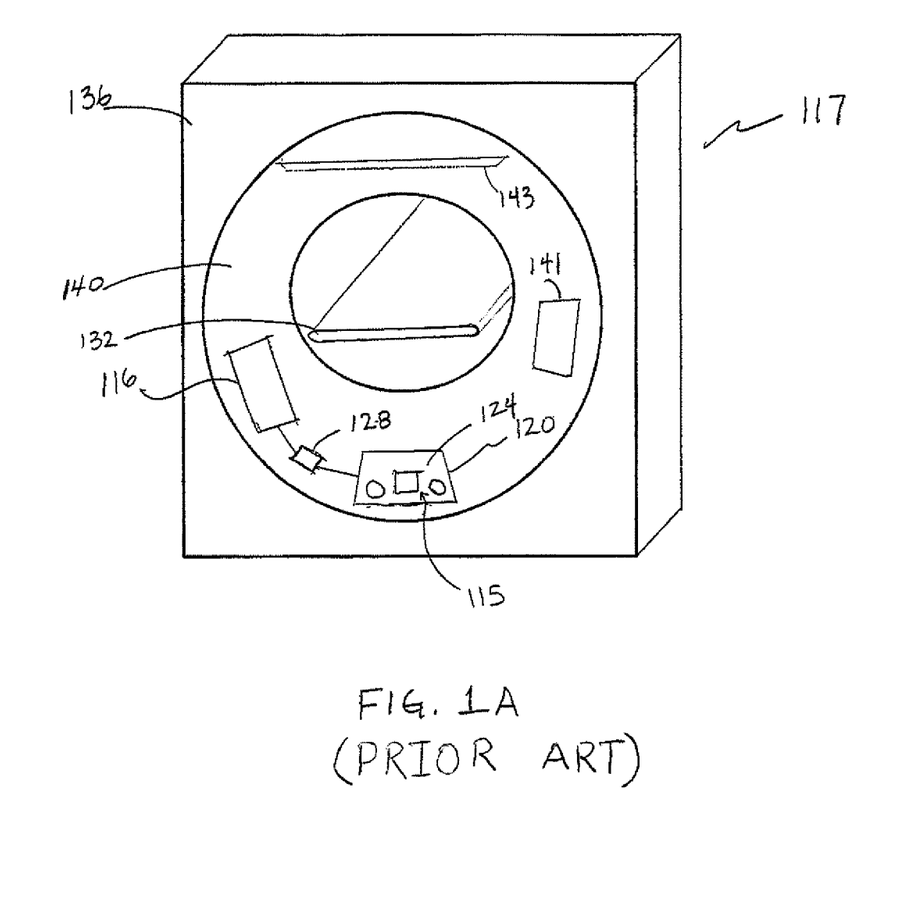
FIG. 1A is a schematic illustration of an example X-Ray generation device of the type to be serviced according to principles of the present invention.
Figure 1B:
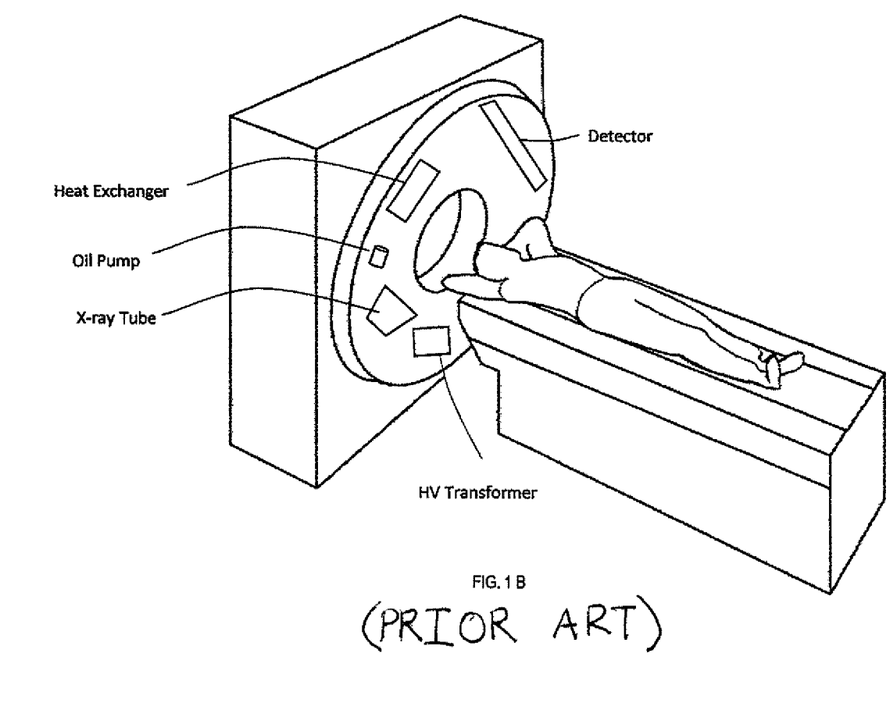
FIG. 1B is an illustration of another example X-Ray generation device of the type to be serviced according to principles of the present invention

As illustrated in an exemplary CT device 117 in FIG. 1, an X-Ray tube assembly generally includes an X-Ray tube, the housing 120 including insulating oil 124, a heat exchanger 116 for removing heat from the insulating oil and pump 128 for circulating insulating oil.

For most X-Ray products, the end of life is primarily predicated by an arcing process. Arcing increases as the insulating oil breaks down. Arcing is a particular problem for CT machines, and when the arcing increases to the point that the machine cannot no longer function, the machine must be removed from patient use. Repair typically requires de-installation of the X-Ray tube assembly partially or in its entirety, including the X-Ray tube, the housing including insulating oil, the pump and the heat exchanger, and associated lead shielding. Such X-Ray Tube Assembly can easily weigh 200-300 lbs. The assembly is then transported or shipped to a processing center and then back to the job site for reinstallation after repair or replacement.

Many scientists believe that long-term reliability of X-Ray tubes can be achieved by taking the degradation characteristics of insulating oil into account in long-term operations which acts as the main factors of the X-Ray tubes' dielectric capabilities. In a view of the present state where many very aged X-Ray tubes are utilized in healthcare centers, the degradation of characteristics of insulating oil needs to be vastly considered. Analysis conducted on aged field insulating oil in X-Ray tubes shows how insulating oil alters and degrades over time and has a significant impact on the electrical characteristics of oil, particularly, breakdown voltages. Studies illustrated that chemical and electrical characteristics such as volume resistivity, dielectric loss tangents, interfacial tensions, and total acid values are degrading with increasing oil age which can be used as markers for identifying aging statuses and diagnose irregularities at early stages before leading to failure. The physical characteristics such as kinetic viscosities, densities, and flash points also change with increasing age but also their change trends depend on the oil type as well. It has been shown that interfacial tension changes with a higher value comparing to the other characteristics of insulating oil and can be used as an effective marker for insulating oil deterioration. To determine the deterioration status of insulating oil, it is vital to study the characteristics of insulating oil of the existing X-Ray tubes in the field. To study the need for changing aged oil frequently, samples of aged insulating oil need to be collected from the field and analyzed for identifying the electrical, chemical, and physical markers that can serve as factors of insulating oil deterioration.

Dielectric breakdown characteristics of insulating oil are affected by presence of foreign objects such as metallic particles, cellulosic fibers, and water contents, due to their effects as electrical charges on electrical fields. Due to the fact that the water content of insulating oil significantly decreases the breakdown voltage of the insulating oil, the water content is commonly recognized as an important diagnostic marker that can be used to determine the status of depreciation of insulating oil. Furthermore, the physical characteristics are subjective to change by hydrocarbon variations. It has been shown that among the physical characteristics of insulating oil, interfacial tension, which is influenced by impurities in oil, varies considerably with increasing age and can be used as an effective marker for detecting deterioration of oil. Chemical changes of oil can generate organic acids, sludge, and water due to the oxidization or radiation deterioration; therefore, degrade the electrical insulation. To sum up, break down voltage as an electrical characteristic, interfacial tension and viscosity as mechanical characteristics, and water content and total acid number as chemical characteristics show good tendencies of change with oil aging and can be utilized as markers for insulating oil deterioration.

All these markers illustrate that improved or proper operation and extending the life of an operating X-Ray tube can be achieved by exchanging aged insulating oil with quality fresh insulating oil in a specific period of time. The present invention provides a system and method for purifying, enhancing and/or exchanging insulating oil of an X-Ray tube on an imaging center.

There is a need to an insulating oil purification and exchange system and corresponding methods for processing "drum" insulating oil, draining aged oil from an X-Ray tube, and filling the X-Ray tube housing with the processed oil in a clean and efficient manner that reduces/eliminates contamination of the insulating oil during the exchange process, the system of which may be portable for use at an imaging center or in situ. Methods according to principles of the present invention are intended to save time and expense resulting from deinstallation of an X-Ray tube housing, typically weighing 200-300 lbs, and heat exchanger from a CT-scanner and, for a portable device, shipping the X-Ray tube assembly to a processing center and then back to the job site.

BRIEF SUMMARY OF THE INVENTION

Accordingly, the present invention is directed to a vacuum oil purification system that obviates one or more of the problems due to limitations and disadvantages of the related art.

An advantage of the present invention is to provide a vacuum oil purification system which allows extending the lives of X-Ray tubes of CT scanners and radiography devices by properly exchanging their insulating oil without any need to de-install the X-Ray tubes and in a short downtime and method for performing the same.

In an aspect of the present invention, a vacuum oil purification system which includes a fresh oil vacuum chamber for degasifying and dehumidifying insulating oil, an old oil vacuum chamber for collecting aged oil using vacuum, a vacuum pump for generating vacuum environment, an oil pump for circulating oil, an oil filter for removing particles from oil, a pressure vessel for generating and adjusting oil pressure, heaters, temperature, pressure and vacuum sensors, a circular modular hose for pointing the oil flow to the wall of the fresh oil chamber, an optional oil penetration tray, a control panel having all the control buttons, LEDs, and quick connects, a mobile platform to hold all components in place, and an oil pan to collect all oil drips. A control unit with an LCD supervises all the input signals from sensors and generates command signals. The fresh oil vacuum chamber is covered by a foam and foil wrap insulation for heat exchange separation. This insulation cover dampens sound and vibration as well. The chambers have oil drain valves at the bottom. Vacuum is generated by a vacuum pump and is controlled manually by a switch and a vacuum gauge for each chamber. The vacuum is also controlled by a vacuum sensor coupled with electronics and the control unit to toggle vacuum pump on and off automatically. The entire system including the electronics may be mounted on a four-wheel platform to facilitate transport to a job site for example a healthcare center. Apparatus for purifying the insulating oil while flushing includes a spin-on filter to clean insulating oil in the return line.

Additional features and advantages of the invention will be set forth in the description which follows, and in part will be apparent from the description, or may be learned by practice of the invention. The objectives and other advantages of the invention will be realized and attained by the structure particularly pointed out in the written description and claims hereof as well as the appended drawings.

To achieve these and other advantages and in accordance with the purpose of the present invention, as embodied and broadly described, in one embodiment, an oil purification system for exchanging oil in an X-Ray tube assembly according to principles of the present invention includes a fresh oil vacuum chamber comprising a fresh oil containment vessel, an oil inlet port and at least one oil outlet port; an old oil vacuum chamber comprising an old oil containment vessel, an inlet port and an outlet port; at least one vacuum pump to generate vacuum inside the fresh oil chamber and the old oil chamber; at least one flow pump to circulate oil toward the X-Ray tube assembly in the imaging system, the flow pump including an inlet and an outlet; at least one oil filter; and at least one heater; and a plurality of configurable fluid flow paths between the fresh oil chamber, the old oil chamber, the flow pump and the X-Ray tube assembly to form one of a plurality of fluid communication circuits for one of processing fresh oil; replacing oil in the X-Ray tube assembly and flushing air bubbles from oil in the X-Ray tube assembly.

In another aspect of the present invention the fluid flow paths are configured to form a closed fluid communication circuit between the fresh oil chamber and the flow pump and a pressure adjustment device, wherein the vacuum pump is connected to the fresh oil chamber to control vacuum in the fresh oil chamber.

In another aspect of the present invention the closed fluid communication circuit comprises an outlet of the fresh oil chamber in fluid communication with the inlet of the flow pump, the outlet of the flow pump in fluid communication with the pressure adjustment device and the pressure adjustment device in fluid communication with an inlet of the fresh oil chamber.

In another aspect of the present invention, wherein the fluid flow paths are configured to form a closed fluid circuit between the fresh oil chamber, the X-Ray tube assembly, and the old oil chamber, wherein the vacuum pump is connected to the old oil chamber to control vacuum in the old oil chamber.

In still another aspect of the present invention, the closed fluid circuit comprises the outlet port of the fresh oil chamber in fluid communication with an inlet of the X-Ray tube assembly; an outlet of the X-Ray tube assembly in fluid communication with inlet port of the old oil chamber.

In another aspect of the present invention, the fluid flow paths are configured to form a closed fluid circuit between the fresh oil chamber, the flow pump, the X-Ray tube assembly and a pressure adjustment device.

In another aspect of the present invention, the closed fluid circuit comprises the outlet of the flow pump in fluid communication with an inlet of the X-Ray tube assembly; an outlet of the X-Ray tube assembly in fluid communication with the inlet port of the fresh oil chamber, with the pressure adjustment device therebetween; and the outlet port of the fresh oil chamber in fluid communication with the inlet of the flow pump.

According to principles of the present invention, A method of replacing insulating oil in an X-Ray tube assembly, comprises processing a supply of fresh oil by heating, degasifying, dehumidifying and filtering the supply of fresh oil and draining and replacing a quantity of aged oil from the X-Ray Tube assembly.

In an aspect of the present invention, the processing the supply of fresh oil comprises heating the fresh oil in a fresh oil drum to a predetermined temperature at a predetermined vacuum state for a predetermined time; and circulating the fresh oil from the fresh oil drum through an oil filter and a flow pump and back to the fresh oil drum by actuating the flow pump.

In an aspect of the present invention, the draining and replacing a quantity of aged oil comprises connecting a fresh oil chamber containing the supply of fresh oil to the X-Ray tube assembly fluidically, connecting the X-Ray tube assembly to an old oil chamber fluidically, and maintaining vacuum in the fresh oil chamber containing the supply of fresh oil at approximately 0-5 in HG vacuum and maintaining vacuum in the old oil chamber at approximately 15-20 inHg vacuum, thereby creating a pressure imbalance between the fresh oil chamber and the old oil chamber such that fresh oil flows from the fresh oil chamber through the X-Ray tube assembly to the oil chamber.

In an aspect of the present invention, the fresh oil is allowed to flow from the fresh oil chamber through the X-Ray tube assembly to the old oil chamber until oil exiting the X-Ray tube assembly is of a predetermined quality In another aspect of the present invention, the method further includes circulating fresh oil through the X-Ray tube assembly by forming a closed fluid circuit by connecting a fresh oil chamber containing the supply of fresh oil to the X-Ray tube assembly fluidically, connecting the X-Ray tube assembly to a flow pump fluidically, and connecting the flow pump to the fresh oil chamber; maintaining a predetermined vacuum in the fresh oil chamber; and maintaining a predetermined pressure in the closed fluid circuit; and causing the fresh oil to flow through the closed fluid circuit for a predetermined period of time.

Further embodiments, features, and advantages of the mobile vacuum oil purification system and methods, as well as the structure and operation of the various embodiments of the mobile vacuum oil purification system and method, are described in detail below with reference to the accompanying drawings.

It is to be understood that both the foregoing general description and the following detailed description are exemplary and explanatory only, and are not restrictive of the invention as claimed.

BRIEF DESCRIPTION OF THE DRAWINGS

The accompanying figures, which are incorporated herein and form part of the specification, illustrate a vacuum oil purification system according to principles of the present invention. Together with the description, the figures further serve to explain the principles of the vacuum oil purification system described herein and thereby enable a person skilled in the pertinent art to make and use the a vacuum oil purification system.

DETAILED DESCRIPTION OF THE INVENTION

Reference will now be made in detail to embodiments of the vacuum oil purification system and methods with reference to the accompanying figures, in which like reference numerals indicate like elements. Different numbers from figure to figure may be used merely for convenience in referring to the figures.

FIG. 1 is a schematic illustration of an X-Ray generation device, e.g., a CT scanner that can be service by a vacuum oil purification system according to principles of the present invention. As can be seen, an X-Ray tube 15 in conjunction with a heat exchanger 116 is installed in a CT scanner 117. The CT scanner consists of a patient table 132 for receiving and positioning patients, a stationary platform 136 in which a gantry 140 is installed for rotation around the patient table. The gantry 140 carries components such as a HV transformer 141, an X-Ray tube 115 combined with a heat exchanger 116 and a radiation detector 143, which are placed inside the gantry 140 rotatable about an examination subject and on opposite sides.

Figure 2:
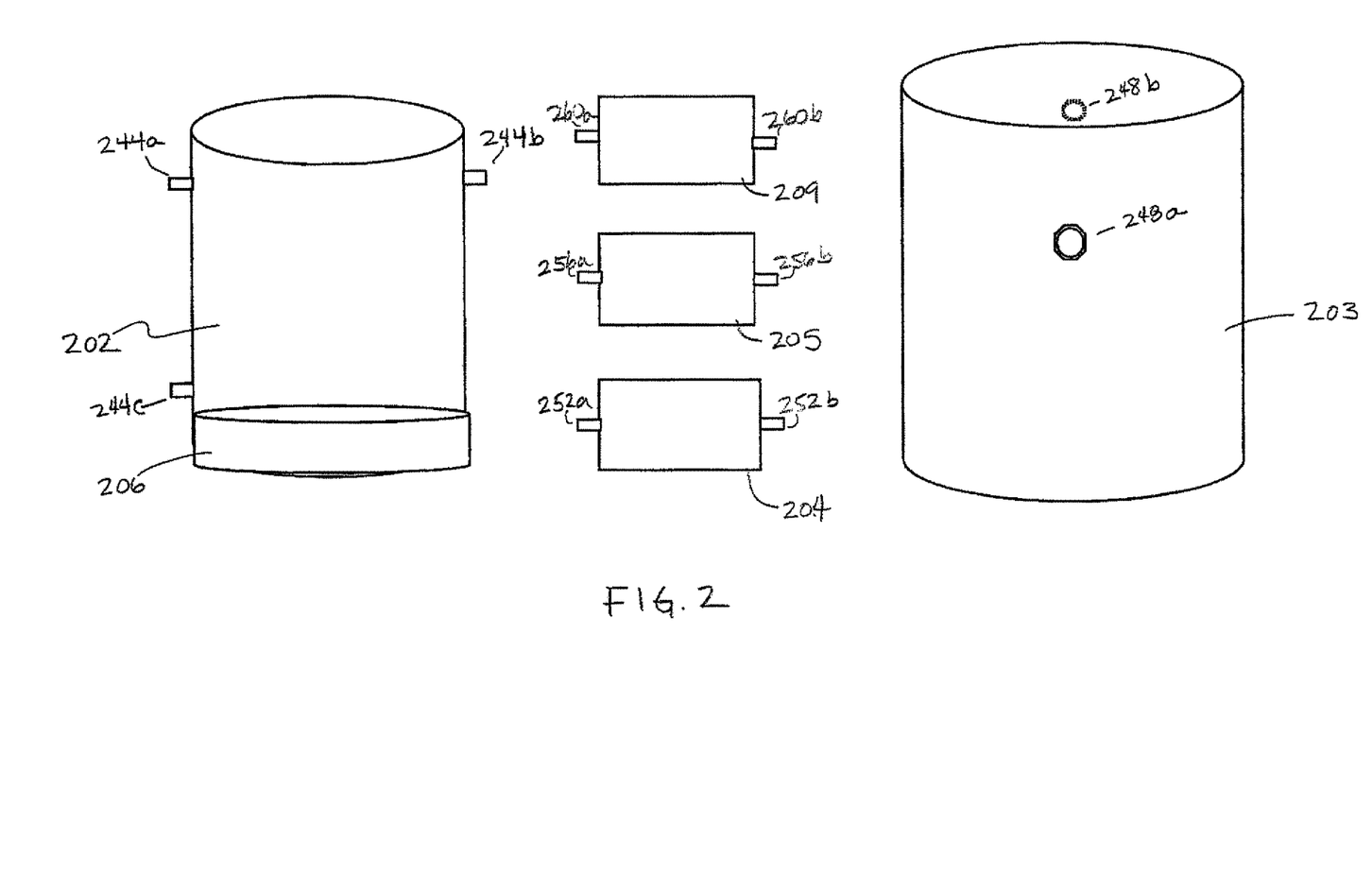
FIG. 2 is a schematic illustration of an embodiment of a vacuum oil purification system according to principles of the present invention.

An embodiment of a vacuum oil purification system according to principles of the present invention is schematically illustrated in FIG. 2. As illustrated, the system includes a fresh oil vacuum chamber 202, an old oil vacuum chamber 203, at least one vacuum pump to generate vacuum inside chambers 202/203, at least one flow pump 205 to circulate oil toward an X-Ray tube (not shown) and back to the system; at least one oil filter 209 and at least one heater 206. One heater may be located under the fresh oil drum and another heater may be located around the fresh oil drum (not shown in FIG. 2). Each of the fresh oil chamber and the old oil chamber includes at least one port 244/248. In some circumstances, a port may be used as an inlet port in some situations and an outlet port in other situations. In the some of the fluid communication circuits described herein, the fresh oil chamber includes two ports and the old oil chamber includes two ports, although not all ports need be in use during any of the disclosed processes. It is within the scope of this invention to have dedicated inlet and outlet ports for each of the components disclosed as part of the fluid communication system described herein, without departing from the spirit and scope of the principles of this invention.

The fresh oil chamber according to an embodiment of the present invention is schematically illustrated in FIG. 2. As can be seen in the illustration, the fresh oil chamber includes a first upper port 244a and a second upper port 244b. In the context of the figure and the description made herein, the first upper port is an upper "left" port and the second upper port is an upper "right" port. Such relative orientation terms are used for convenience of description, and one of skill in the art that the principles of the present invention are not limited to "left" and "right" relative orientation of the described ports. "Upper" in the context of the fresh oil chamber of the present embodiment means that the ports are located in the wall of the chamber above the midline of the chamber. The fresh oil chamber according to the present embodiment also includes a "bottom" port 244c. "Bottom" in the context of the fresh oil drum of the present embodiment means that the ports are located in the wall of the chamber below the midline of the chamber.

The old oil chamber according to an embodiment of the present invention is schematically illustrated in FIG. 2. As can be seen in the illustration, the old oil chamber may include a first port 248a and a second port 248b. In the context of the figure and the description made herein, the first port is a "front" port and the second port is a "rear" port. Such relative orientation terms are used for convenience of description, and one of skill in the art that the principles of the present invention are not limited to "front" and "rear" relative orientation of the described ports.

Also illustrated in FIG. 2 are at least one vacuum pump 204 to generate vacuum inside chambers 202/203 and an oil filter 209. The system may further include a flow pump 205 configured to promote oil communication between the fresh oil chamber 202, the old oil chamber 203 (or both) and the X-Ray tube assembly (100 in FIG. 1).

Each of the vacuum pump, the flow pump and the oil filter includes at least two ports for inclusion in the fluid communication circuits according to principles of the present invention. Vacuum pump 204 includes port 252a and port 252b; flow pump 205 includes port 256a and port 256b; and oil filter 209 includes port 260a and port 260b. All of the ports may use "quick connect" fittings to promote ease of use of the system when connecting various fluid communication circuits according to principles of the present invention.

The old oil chamber is a vacuum chamber for collecting collect used (aging) oil from an X-Ray tube utilizing a vacuum. The vacuum is provided by the vacuum pump. The old oil chamber includes an oil containment vessel made of any suitable material, including, but not limited to, aluminum, in any suitable shape, including but not limited to cylindrical. In experiments, the old oil chamber used comprised 15 gallons, but is not limited to such size. The old oil chamber should be configured according to the amount of oil contained in the X-Ray tube assembly plus an amount of oil used for flushing the assembly in accordance with the method according principles of the present invention, as are described herein.

The system further includes a fresh oil chamber that includes an oil containment vessel. The fresh oil containment vessel may be made of any suitable material, including, but not limited to aluminum in any suitable shape, including but not limited to cylindrical. In experiments, the fresh oil chamber containment vessel used comprised 15 gallons, but is not limited to such size. The vacuum pump, if only one is used, is placed such that it can provide a vacuum to both the fresh oil chamber and the old oil chamber, such as between the fresh oil chamber and old oil chamber to have better access to both chambers. Such connection may be static-dissipative PVC clear tubing or other tubing capable of sustaining a suitable vacuum in the fresh oil chamber and old oil chamber and the associated fluid circuit.

Figure 3:
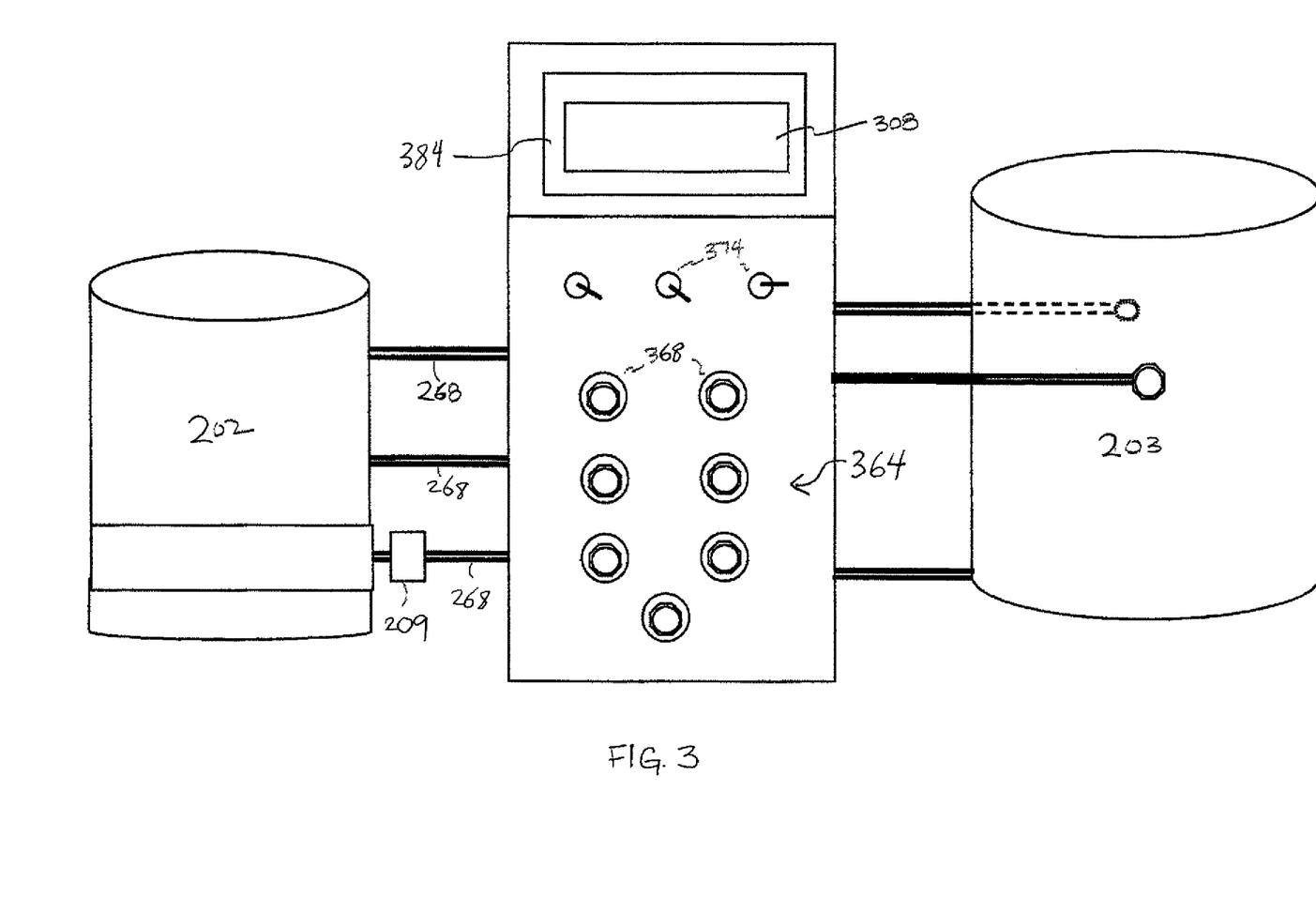
FIG. 3 is a schematic illustration of aspects of an embodiment of a vacuum oil purification system according to principles of the present invention.

As illustrated in FIG. 3, the system may include a "port panel" 364 that allows for easy connection to any of the ports of the various components of the present invention. The port panel may include quick connect fittings 368 to allow for an operator to easily remove connections to the external X-Ray tube assembly and between components of the system during processes according to principles of the present invention, as described in more detail below. For example, the inlet and outlet ports of the various components may be directly connected to the "port panel" for providing easy access to the various ports during operation. The system may further include toggle switches 374 to turn on and off various components to start or end operation of the various components, such as the vacuum pump, heater, or flow pump. Such exemplary toggle switches may be located on the port panel as illustrated in FIG. 3, but such switches may be located elsewhere in the system, as would be appreciated by one of skill in the art.

Figure 4:
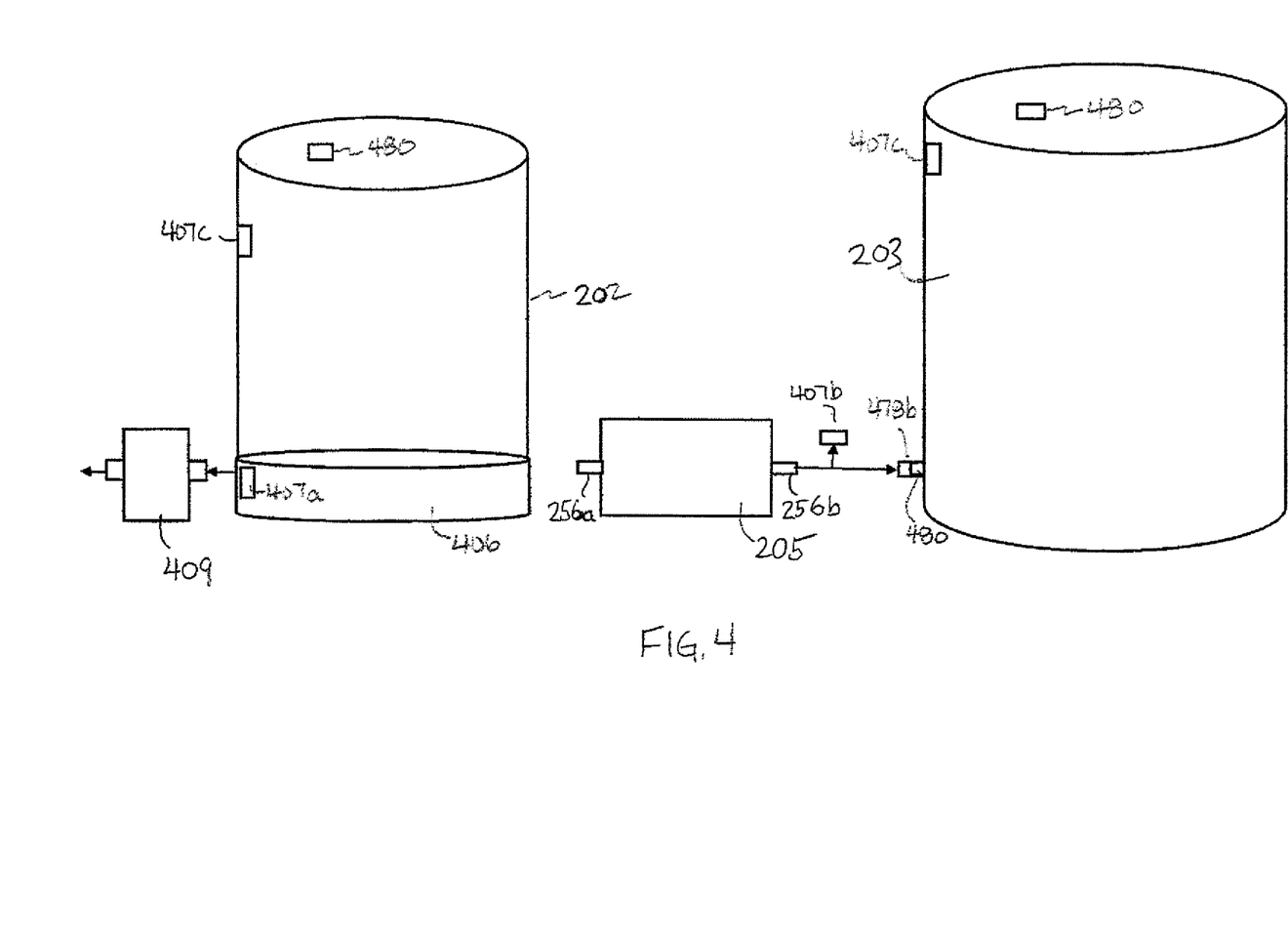
FIG. 4 is a schematic illustration of temperature, pressure, and vacuum in conjunction with the controlling module.

As illustrated in FIG. 4, the system may also include a plurality of sensors 407, which may include temperature, pressure and vacuum sensors (407a, 407b, 407c). The system may further include at least one, e.g., three, solenoid valve 480. The system may further include a control module and a display (shown in FIG. 3 as 384 and 308, respectively). The system may optionally include a sampler system installed in at an appropriate location in the waste oil line; toggle switches for manual control; and a pressure adjustment tool. The fresh oil vacuum chamber includes inlets and outlets, as described above, a lid sealed by a gasket, a vacuum gauge and modular hoses for directing oil flow. The lid may be formed of any suitable material, such as a polycarbonate. The pressure tool may comprise a pressure gauge and a pressure control valve. The at least one solenoid valve 480 may be part of a safety set up in which, if pressure in the system increases to more than a predetermined level, e.g., 20 psi, the solenoid valve opens to release pressure from the system. The sampler system may include an oil reservoir or receptacle with an inlet and two outlets, ball valves, and a shortcut line. The control module monitors temperature, vacuum and pressure levels and provides indicators of such levels on the display. The control module may include a graphical user interface to allow a user to access and update the system, which may include touch screen controls. In the alternative, the system may include digital or analog gauges and manual digital or analog controls.

Figure 5:
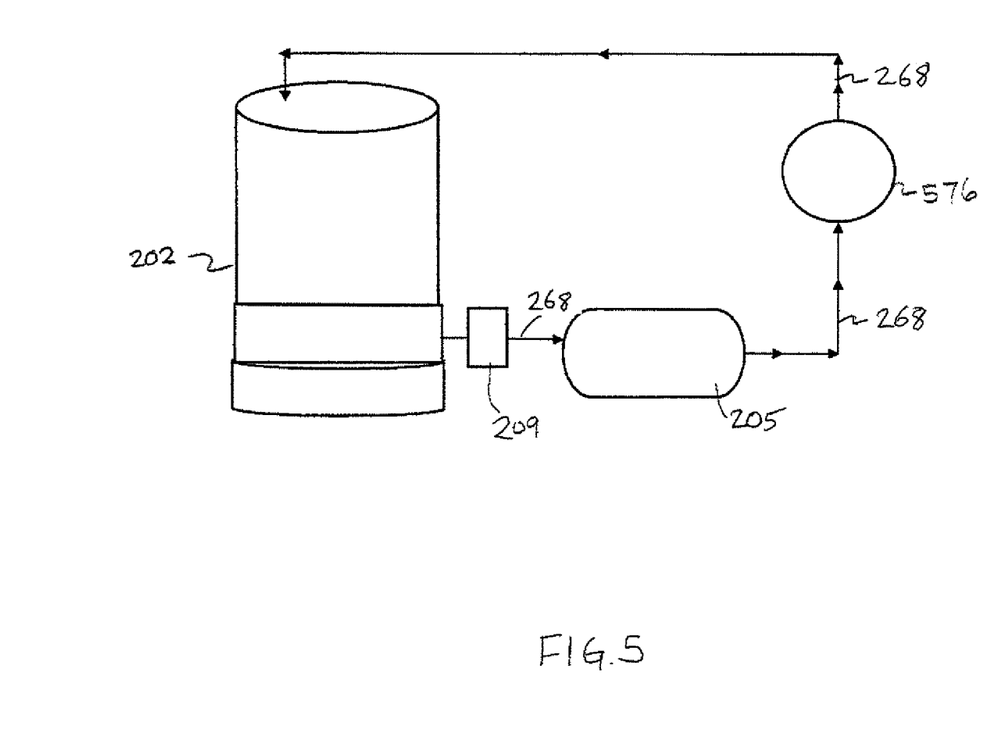
FIG. 5 is a schematic illustration of a configuration of the purification system in a processing phase according to principles of the present invention.

Referring to FIG. 5, the method of the present system includes three phases of operation. It is intended that all three phases be performed at the operating location of the X-Ray generating system, although such convenience is not required. The three phases include a processing phase, a drain phase and a flush phase. At least the processing phase may be performed prior to arrival at the operating location, but is not required, and performing the processing phase at the operating location may be more appropriate. During the processing phase, fresh oil is heated to a predetermined temperature at a predetermined vacuum state. In some aspects, the fresh oil is filtered during the processing phase, but may be "pre-filtered" before reaching the operating location. Assuming that the fresh oil chamber 202 starts at ambient conditions, an outlet of the fresh oil chamber 202 is connected to an inlet of a flow pump 205. An outlet of the flow pump 205 is connected to an inlet of a pressure adjustment device 576, such as a ball valve connected to at least two quick connects monitored by a pressure gauge, an outlet of which is connected to an inlet of the fresh oil chamber, to create a closed-fluid circuit that can adjust vacuum pressure within the fresh oil chamber 202, as described further below. The flow pump 205 is turned on for a predetermined period of time, e.g., at least 10 minutes to cause the fresh oil to flow within the closed fluid circuit. After the fresh oil has flowed within the closed circuit for at least 10 minutes, the flow pump 205 is turned off. 28 inHG of vacuum level (negative pressure) is pulled in to the fresh oil chamber 202 for at least 30 mins under operating temperature of 150-170° F. Then the vacuum level in the fresh oil chamber 202 is reduced to a value less than 22 in HG and more than 15 in HG via the vacuum, release ball valve. The flow pump 205 is turned on for at least 30 minutes and the pressure of oil into the return line to the fresh oil chamber 202 is adjusted using the pressure adjustment kit 576 to 5-10 psi. After 30-60 minutes, the flow pump 205 is turned off and the vacuum reduced to 15-20 inHg. During the exemplary processing phase, the oil is heated to a temperature of 140-170 degrees F.

Figure 6:
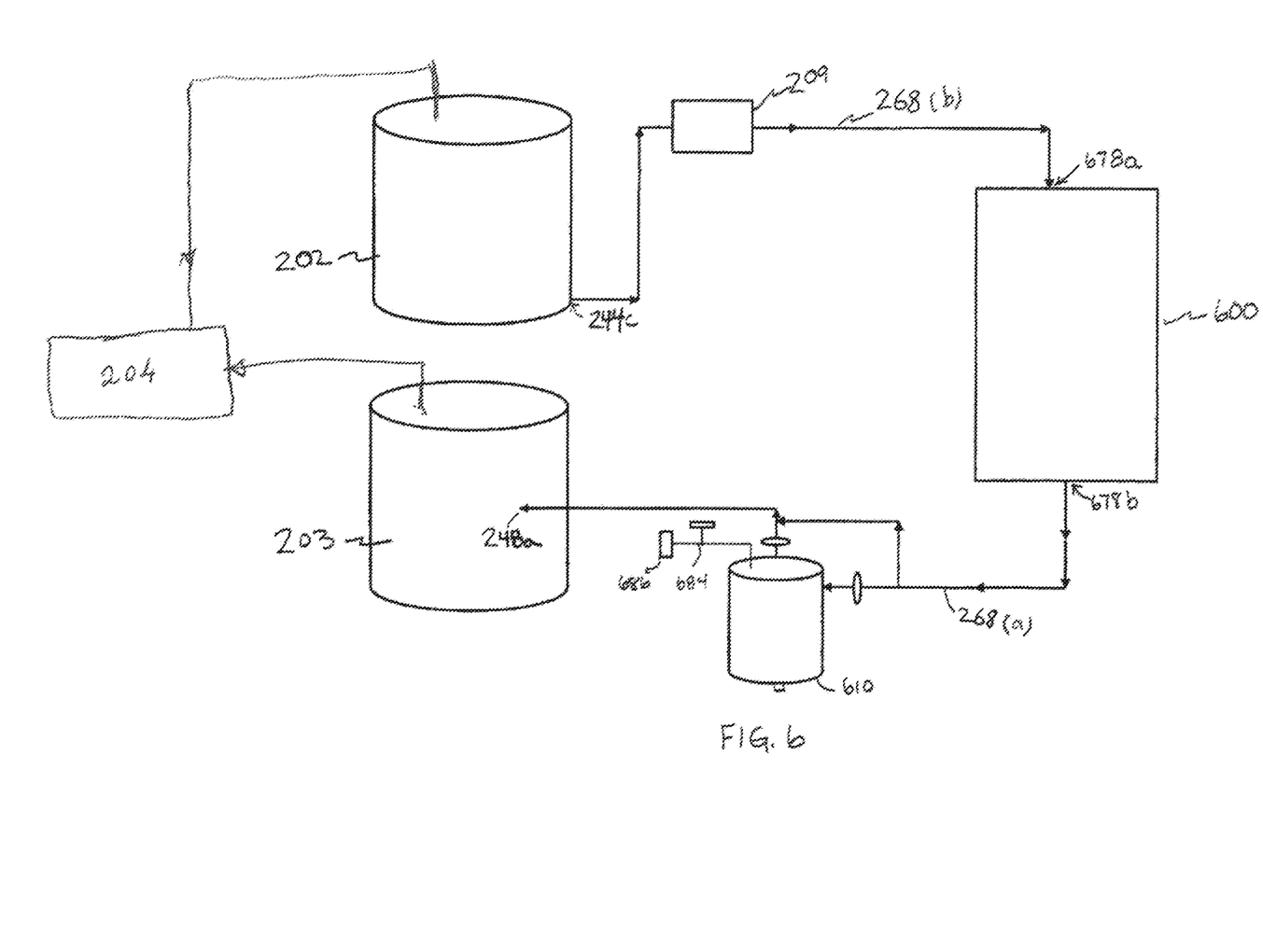
FIG. 6 is a schematic illustration of a configuration of the purification system in a drain phase according to principles of the present invention.

Referring to FIG. 6, before the drain phase, the vacuum inside the fresh oil chamber 202 is completely released, the fresh oil chamber 202 is connected to an inlet 678a of the X-Ray lube assembly 600 passing the oil filter 209, and the old oil chamber 203 connected to an outlet 678b of the X-Ray tube assembly 600 to allow fluid communication from the fresh oil chamber 202 through the X-Ray tube assembly 600 to the old oil chamber 203. The hoses 268 are filled with old oil before starting the drain phase. The vacuum pump 204 (FIG. 6) is used to generate vacuum into the fresh oil vacuum chamber and old oil vacuum chamber 203 through its permanent connections to these chambers. During the drain phase, the fresh oil chamber 202 is maintained at approximately 0-5 inHg vacuum and the old oil chamber 203 is maintained at approximately 15-20 inHg vacuum, thus creating a pressure imbalance between the two chambers 202/203 that causes the fresh oil to be pulled into the X-Ray tube assembly 600 as the aged insulating oil within the X-Ray tube assembly 600 is drawn into old oil chamber 203. The relative pressures of the fresh oil chamber 202 and the old oil chamber 203 here are exemplary, and may be varied as long as an appropriate pressure imbalance is created to support drawing of oil from the fresh oil chamber 202 through the X-Ray tube assembly 600 into the old oil chamber 203. The vacuum in each of the fresh oil chamber 202 and the old oil chamber 203 are controlled by the vacuum pump (or two separate vacuum pumps) 204. In the exemplary embodiment of FIG. 6, the fresh oil chamber 202 is connected to the X-Ray Assembly via the bottom port 244c of the fresh oil chamber 202 and an inlet port 678a of the X-Ray tube assembly 600. The connection may be made directly using a hose or via a port panel with quick connect fitting as previously described, or any other means as would be appreciated by one of skill in the art. In the same exemplary embodiment if FIG. 6, the old oil chamber 203 is connected to an outlet port 678b of the X-Ray tube assembly 600 via the front port 248a of the old oil chamber 203. The connection may be made directly using a hose or via a port panel with quick connect fitting as previously described, or any other means as would be appreciated by one of skill, in the art.

A sample collection receptacle/reservoir 610 (e.g., a bottle or the like) may be placed in line between the X-Ray tube assembly 600 and the old oil chamber 203 to allow collection of the oil being drained from the X-Ray tube assembly 203. The sample collection receptacle 610 may be connected to the fluid conduit (e.g., hose) via a closable valve or valves such that the oil may be sampled at a particular time and the remaining oil allowed to flow unimpeded or the flow may be stopped, the receptacle filled and oil flow resumed. The sample collection reservoir 610 may be removable such that when the valve is closed, the sample reservoir 610 may be removed and replaced to allow for multiple samples to be collected at different times during the drain phase. Samples may be tested by portable equipment on site or off site using conventional methods. The optional sample collection feature of the present embodiment is illustrated in FIG. 6. An exit port is mounted at the bottom of the sample reservoir to collect the sampled oil. A ball valve 684 connected to an air filter 686 is used to balance the pressure inside the sample reservoir to allow the sampled oil to drain faster from the exit port at the bottom of the sample reservoir.

The drain phase continues until the oil exiting the outlet of the X-Ray tube assembly 600 reaches a predetermined level of quality. Such predetermined level of quality can be determined by visual inspection of the color of the oil. For example, when aged oil exits the X-Ray tube assembly 600, it is may be a dark brown color, such as the color of root beer or cola. Fresh oil being used to replace the aged oil is typically a yellow color. When the oil exiting the X-Ray tube assembly 600 is yellow, roughly matching the color of the fresh oil being supplied, the X-Ray tube assembly 600 can be considered sufficiently drained. Alternatively, the oil exiting the X-Ray tube assembly 600 may be sampled using the sampling receptacle 610 and tested to confirm that the oil exiting the X-Ray tube assembly 600 is of sufficient quality to conclude the draining process/phase of the process. If the X-Ray generating system being serviced is a CT scanner, the CT scanner may be rotated during the drain phase and introduction of fresh oil.

Figure 7:
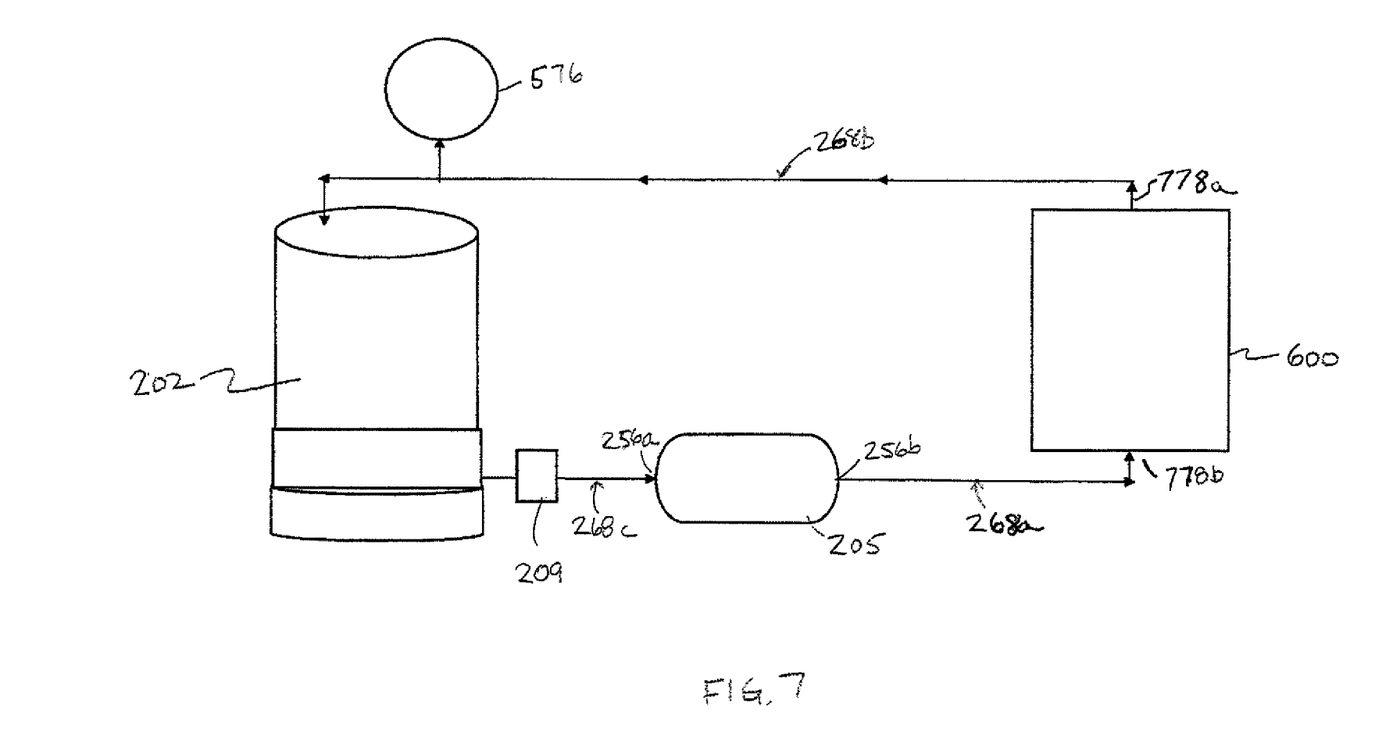
FIG. 7 is a schematic illustration of a configuration of the purification system in a flush phase according to principles of the present invention.

Referring to FIG. 7, after the drain, phase is concluded, the X-Ray tube assembly 600 is flushed/purged using fresh oil chamber to remove the possible air pockets from the X-Ray tube assembly and also adjust the amount and pressure of the oil inside the X-Ray tube assembly, in the flush phase, the fresh oil chamber 202 is set to approximately −15-20 in HG vacuum. A port 256a of the flow pump 205 is connected to tire oil lifter 209 and in fluid communication with an inlet port 778b of the X-Ray tube assembly via a first hose 268a. An outlet port 778a of the X-Ray tube assembly 600 is connected to and in fluid communication with an inlet 244a of the fresh oil chamber 702-202 via a second hose 268b, with a pressure adjustment device/kit 576 in the fluid line there between which is used to adjust the pressure of the oil inside the X-Ray tube assembly during flushing. The fresh oil chamber 202 is connected to and in fluid communication with an inlet 256a of the pump via a third hose 268c. Thus, the fresh oil chamber 202. X-Ray tube assembly 600 and the flow pump 205 form a closed fluid circuit. The flow pump 205 is turned on as soon as possible after the fluid circuit has been closed. The pressure in the closed fluid circuit is adjusted via the pressure adjustment device to approximately 5-10 psi. The flow pump 205 is operated for approximately 30 minutes. The flow pump 205 is then turned off and the second hose 268b and the first hose 268a are then disconnected in turn. During the flush phase, temperature of the fresh oil circulating is maintained at approximately 150-170° F. If the device is a CT machine and the X-Ray tube is installed on its gantry, the gantry is rotated 60 degrees every 5 minutes during flushing to allow air pockets pulled out from the assembly.

The X-Ray tube assembly 600 is then allowed to cool to room temperature. An amount of oil is allowed to remain, in the first hose 268a and the second hose 268b, and the open ends of the first hose 268a and the second hose 268b are elevated to be above the level of the X-Ray tube assembly 600 to allow fresh oil to drain back into the X-Ray tube assembly 600 if required because of the oil contraction.

Figure 8:
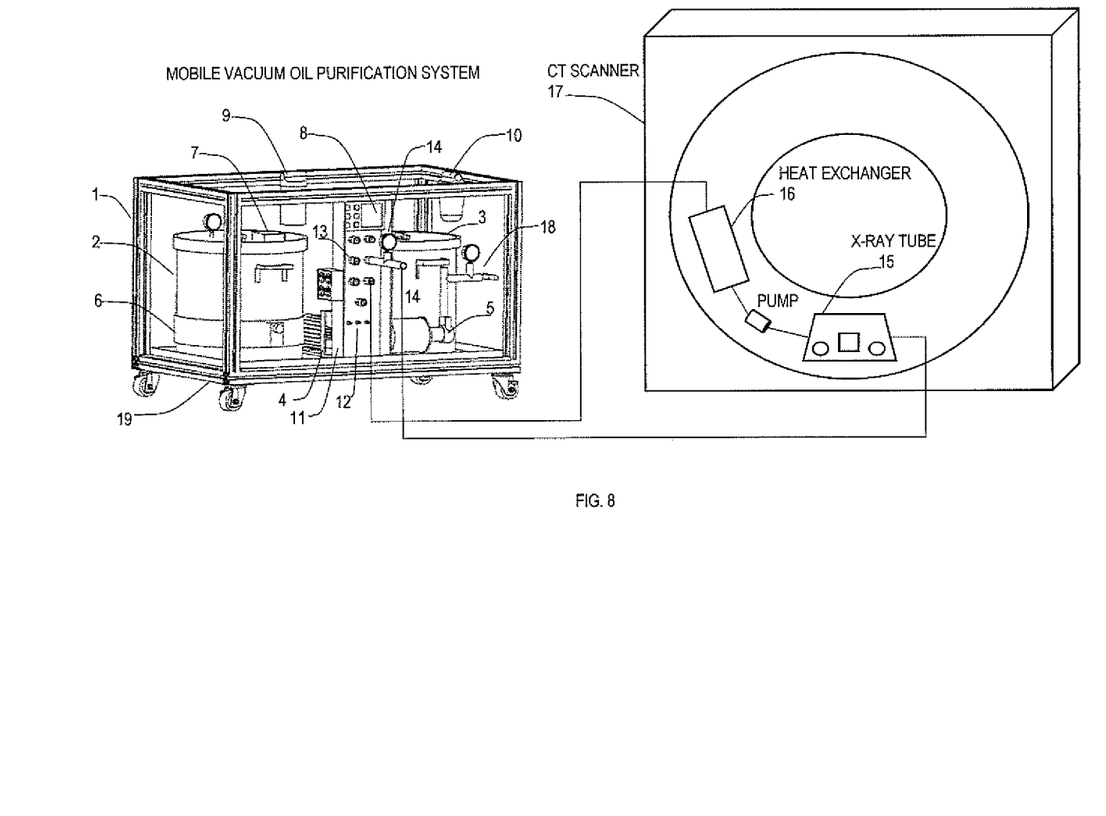
FIG. 8 is a schematic illustration of a mobile embodiment of the vacuum oil purification system according to principles of the present invention in association with a computer tomography (CT) scanner of conventional design.

An exemplary embodiment of a mobile vacuum oil purification system according to principles of the present invention is illustrated in FIG. 8 and is described below.

An aluminum platform 19 with caster lifting wheels 1 for assembling all the components and carrying to sites, a fresh oil vacuum chamber 2 to maintain and process fresh oil, an old oil vacuum chamber 3 to hold aged oil after pumping out an X-Ray tube assembly, a vacuum pump 4 to generate vacuum inside the fresh oil vacuum chamber 2 for processing purposes as well as generate vacuum inside the old oil vacuum chamber 3 to drain the aged oil from the outlet of the X-Ray tube assembly 15 during the draining phase, a flow pump 5 to circulate the processed insulating oil from the fresh oil vacuum chamber 2 toward the X-Ray tube assembly and to one of the chambers 2, 3 as well as flow oil during the oil processing phase, heaters 6 to heat up the insulating oil at the fresh oil vacuum chamber up to 160° C., sensors 7 to monitor temperature, pressure and vacuum levels, a control module with touch-screen LCD 8, to control and program the process algorithms, an oil filter 9 to remove external particles from the oil. A sampler system 10 is designed to take sample of old oil for chemical, electrical and physical analyses. The platform had a panel 11 including manual control keys 12, fittings 13, and the touch-screen LCD. A pressure adjustment tool 14 is used for regulating the pressure of the oil while processing the oil and flushing the X-Ray tube assembly. A graphical user interface (GUI) is programmed to allow a field service engineer to activate the automatic operations of the system as well as change the system parameters such as processing period, flushing period, and safety alarm points. An independent safety setup 18 is added to the system in order to change the direction of the oil to the old oil chamber in case the interior pressure of the X-Ray tube assembly passes a safety pressure level.

FIG. 8 is a schematic illustration of an embodiment of the mobile vacuum oil purification system, this invention, shown in association with an X-Ray tube 15 in conjunction with a heat exchanger 16 installed on a CT scanner 17. The CT scanner consists of a patient table for receiving and positioning patients, a stationary platform in which a gantry is installed for rotation around the patient table. The gantry carries components such as a transformer, an X-Ray tube combined with a heat exchanger and a radiation detector, which are placed inside the gantry rotatable about an examination subject and on opposite sides. The X-Ray tube generates radiation passing through the subject assigned for imaging and installed on the gantry for the purpose of revolution. The detector assembly includes an array of detectors with purpose of changing radiation to electrical signals.

A control unit with a touch-screen LCD 8 may be provided and supervises the input signals from sensors and generates command signals. Additionally, in the exemplary embodiment of FIG. 8, the fresh oil vacuum chamber 2 is covered by a foam and foil wrap insulation for heat exchange separation. This insulation cover dampens sound and vibration as well. The chambers have inlets, outlets, and oil drain ports in the bottom.

In operation of the exemplary embodiment of FIG. 8, a vacuum is generated by a vacuum pump 4 and is controlled manually by a switch and a vacuum gauge for each chamber 2, 3. The vacuum is also controlled by a vacuum sensor 7 coupled with electronics and the control unit to toggle vacuum pump 4 on and off automatically. The entire system including the electronics is mounted on a four-wheel platform 19 to facilitate transport to a job site for example a healthcare center. Apparatus for purifying the insulating oil while flushing includes a spin-on oil filter with 3-9 micron holes cartridge to clean insulating oil in the return line. The filter's head can be aluminum and seals from oil resistance material such as Buna-N. The Cartridge housing is steel. An oil sampler system 10 is designed to take a sample of aging oil during draining from an X-Ray tube.

Verifying that such an oil exchange system can effectively elevate the breakdown voltage of insulating oil is required before allowing the application of the system on an X-Ray tube. For regulating all environmental conditions inside the fresh oil vacuum chamber for processing the oil, a 900 MHz quad-core ARM Cortex-A7 CPU with IGB RAM was used to operate a graphical user interface (GUI) via a Tkinter program or a GTK program. By incorporating both hardware and software, CPUs are used as processors and decision makers in nearly all autonomous devices, from electronics to cars to medical devices. Physical conditions inside the vacuum chambers were detected by sensors and sent to the control module.

The control module compares the received sensor signals with predetermined thresholds and sends control signals to other components of the system to conduct their actions for regulating those conditions. For example, the control module collects data from the temperature, pressure, and vacuum sensors at a rate of one per second. A rotary vane pump was used to circulate the oil based on the program and through its inlet and outlet quick-connects on the front panel. A two stage vacuum pump is toggles on and off by the control module to generate the vacuum inside the chambers. Additionally, two heaters are designed to maintain the accurate temperature of the oil during processing.

Figure 9:
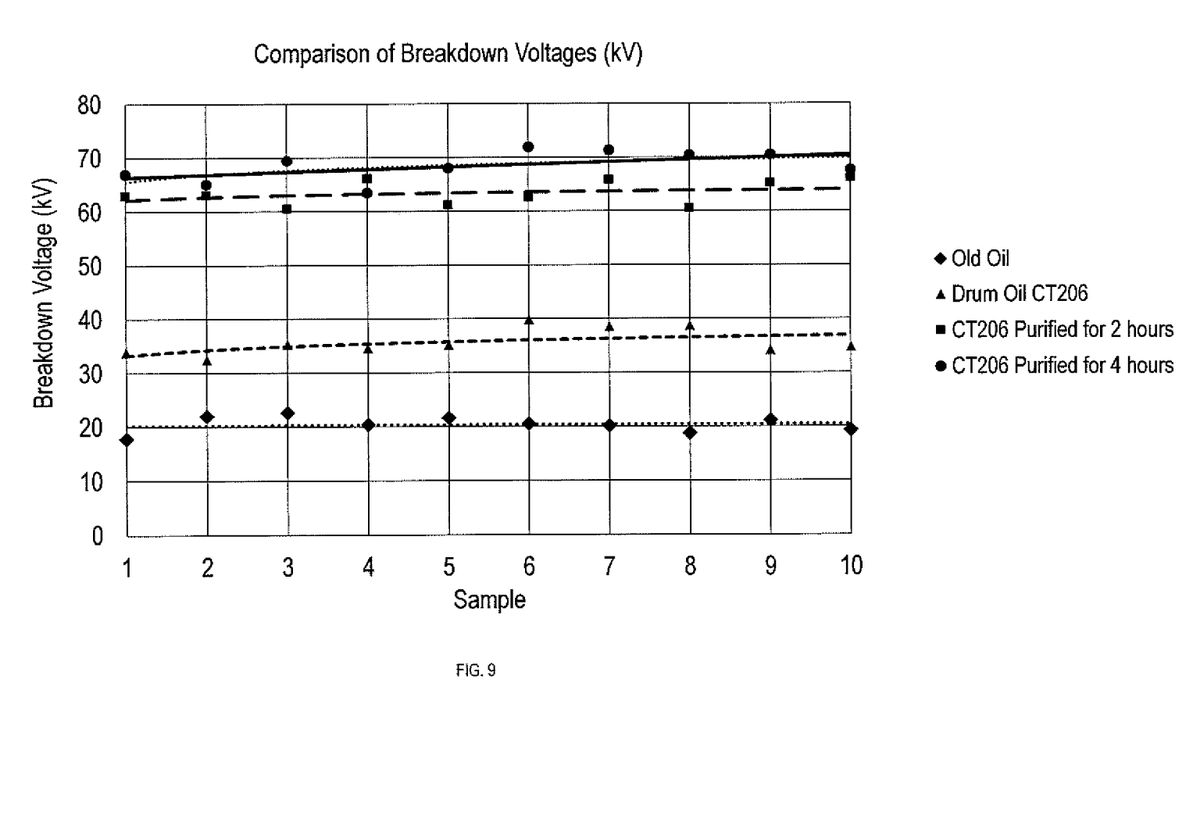
FIG. 9 is a graph showing a comparison among the dielectric breakdown strength of insulating oil at different stages measured according to ASTM D 1816, 2 mm gap standard using VDE electrodes.

A preliminary study was performed on three stages of CrossTrans 206 insulating oil including fresh oil, X-Ray tubes' aging oil (aged more than 400K scan seconds) and fresh oil processed using the mobile vacuum oil purification system. FIG. 9 shows a comparison among the average breakdown voltage of the Crosstrans 206 insulating oil at different stages including purified oil after 4 hours, purified oil after 2 hours, fresh drum oil, and aging oil (aged more than 400K scan seconds). The results show that by processing using the mobile vacuum oil purification system the breakdown voltage of CrossTrans 206 oil measured according to ASTM D1816, 2 mm gap standard using VDE electrodes is 63±2 kV and after 4 hours is 68±3 kV. This value is nearly two fold larger than the average breakdown voltage of fresh drum CrossTrans 206 oil (36±2 kV) measured using the same standard. This shows the significance of processing the insulating oil using the mobile vacuum oil purification system before exchanging the oil of an X-Ray-tube. Furthermore, the average breakdown voltage of aged oil sampled form X-Ray tubes with operation life more than 400K scan seconds is 21±2 kV which is much less than the quality threshold of insulating oil (50 kV) and can lead to electrical short-circuit inside an X-Ray tube which is called arcing.

The above data demonstrate that such an oil exchange system can provide effective processing of insulating oil including dehumidification, degasification, and filtration to enhance the breakdown voltage of insulating oil significantly. Additionally, the developed methods applied to fill an X-Ray tube using the processed oil concurrent to draining the aged oil and later purging the X-Ray tube in a vacuum environment will extend the life of the processed X-Ray tube.

The design of the mobile vacuum oil purification system described herein is highly innovative. With two vacuum-compatible chambers, one designed for degasifying and dehumidifying insulating oil, and the second one designed for draining the aging oil from an X-Ray tube using vacuum, the oil purification system described herein is designed to extend the lives of X-Ray tubes of commercial CT scanners or radiography imagers. The current invention, together with its purposes, capabilities, and advantages thereof, will be best comprehended from the following explanation, and the accompanying drawing.

Conventional oil exchange systems typically restrict the ability and methods to change the insulating oil of X-Ray tubes in a short time on an imaging center and without exposing the interior space of an X-Ray tube to air and therefore humidity. Previous oil exchange apparatuses (for example see the invention described in U.S. Pat. No. 6,254,272 B1 entitled "method and apparatus for extending the life of an X-Ray tube" by Maurice D. Dilick) are limited by their by their lack of consistent temperature, vacuum and pressure conditions inside the fresh oil vacuum chamber. Also previous methods do not provide a threshold for breakdown voltage of processed oil before filling/flushing. They don't include an old oil vacuum chamber to simultaneously drain the aging oil from an X-Ray tube's outlet and pull in the processed fresh oil through the inlet of the X-Ray tube; as a result X-Ray tube will need more processing to remove humidity and condensation. In addition, previous systems have longer preparation time because they are not designed as a portable platform on wheels. Furthermore, sampling vessel is missing from available oil exchange systems. Compared to existence mythologies, the mobile vacuum oil purification system described herein offers a combined approach that takes full advantage of processing insulating oil by enabling dynamic dehumidification, degasification and filtration in a self-regulated and maintained vacuum environment in order to extend the lives of X-Ray tubes.

While various embodiments of the present invention have been described above, it should be understood that they have been presented by way of example only, and not limitation. It will be apparent to persons skilled in the relevant art that various changes in form and detail can be made therein without departing from the spirit and scope of the present invention. Thus, the breadth and scope of the present invention should not be limited by any of the above-described exemplary embodiments, but should be defined only in accordance with the following claims and their equivalents.

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents.

What is claimed is:

1. An oil purification system for exchanging oil in an X-Ray tube assembly in an imaging system, the oil purification system comprising:
   a fresh oil chamber comprising a fresh oil containment vessel, an oil inlet port and an oil outlet port the outlet port of the fresh oil chamber in fluid communication with a first hose for connection with the X-Ray assembly;
   an old oil chamber comprising an old oil containment vessel, an inlet port and an outlet port, the inlet port of the old oil chamber in fluid communication with a second hose for connection with the X-Ray assembly;
   at least one vacuum pump in direct fluid communication with the fresh oil chamber and the old oil chamber to generate vacuum inside the fresh oil chamber and the old oil chamber;
   at least one flow pump in fluid communication with the second hose to circulate oil toward the X-Ray tube assembly in the imaging system, the flow pump including an inlet and an outlet; and
   at least one oil filter in fluid communication with the fresh oil chamber and the first hose;
   wherein the oil purification system is configured to maintain, in a vacuum state, each of the fresh oil chamber, the old oil chamber, the flow pump, the oil filter and the X-ray tube assembly.

2. The system of claim 1, further comprising at least one fluid flow path that forms a fluid communication circuit between the fresh oil chamber and the flow pump and a pressure adjustment device.

3. The system of claim 2, wherein the fluid communication circuit comprises a closed fluid communication circuit comprising an outlet of the fresh oil chamber in fluid communication with the inlet of the flow pump, the outlet of the flow pump in fluid communication with the pressure adjustment device and the pressure adjustment device in fluid communication with an inlet of the fresh oil chamber.

4. The system of claim 1, comprising a fluid flow path between the fresh oil chamber, the X-Ray tube assembly, and the old oil chamber.

5. The system of claim 4, wherein the fluid flow path is a closed fluid circuit comprising the outlet port of the fresh oil chamber in fluid communication with an inlet of the X-Ray tube assembly; an outlet of the X-Ray tube assembly in fluid communication with inlet port of the old oil chamber.

6. The system of claim 1, farther comprising a fluid flow path between the fresh oil chamber, the flow pump, the X-Ray tube assembly and a pressure adjustment device.

7. The system of claim 6, wherein the fluid flow path is a closed fluid circuit comprising the outlet of the flow pump in fluid communication with an inlet of the X-Ray tube assembly; an outlet of the X-Ray tube assembly in fluid communication with the inlet port of the fresh oil chamber, with the pressure adjustment device therebetween; and the outlet port of the fresh oil chamber in fluid communication with the inlet of the flow pump.

8. The system of claim 1, further comprising:
   a port panel comprising a plurality of quick-release fittings, each of the quick release fittings in fluid communication with a respective one of the fresh oil chamber, the flow pump; and the old oil chamber.

9. The system of claim 1, further comprising a control panel, the control panel including a display device to display a plurality of sensor information and a graphical user interface (GUI) to start processes and to update parameters of the system.

10. The system of claim 1, further comprising a portable platform, the portable platform supporting the fresh oil chamber; the old oil chamber; the at least one vacuum pump; the at least one flow pump; the at least one oil filter; and at least one heater.

11. The system of claim 1, where in the at least one vacuum pump is between the fresh oil chamber and the old oil chamber.

12. The system of claim 1, further comprising a heater in thermal communication, with the at least one of the fresh, oil containment vessel and the old oil containment vessel.

13. The system of claim 1, further comprising at least one fluid, flow path between, the fresh, oil chamber, the old oil chamber, the flow pump and the X-Ray tube assembly to form one of a plurality of fluid communication circuits for one oil processing fresh oil; replacing oil in the X-Ray tube assembly; or flushing air bubbles from oil in the X-Ray tube assembly.

14. The system of claim 13, wherein the first hose and the second hose provide the at least one fluid flow path between the fresh oil chamber, the old oil chamber, the flow pump and the X-Ray tube assembly to form one of a plurality of fluid, communication circuits for one of: processing fresh oil; replacing oil in the X-Ray tube assembly; or flushing air bubbles from oil in the X-Ray tube assembly.

15. The system of claim 1, further comprising a heater for heating the fresh oil chamber.

* * * * *